(12) United States Patent
Chow et al.

(10) Patent No.: US 7,812,034 B2
(45) Date of Patent: Oct. 12, 2010

(54) METHOD OF USING PROTEASE INHIBITORS FOR THE TREATMENT OF LIPOSARCOMAS

(75) Inventors: Warren Chow, Pasadena, CA (US); Chu-Chih Shih, Arcadia, CA (US)

(73) Assignee: City of Hope, Duarte, CA (US)

( * ) Notice: Subject to any disclaimer, the term of this patent is extended or adjusted under 35 U.S.C. 154(b) by 1690 days.

(21) Appl. No.: 10/979,851

(22) Filed: Nov. 2, 2004

(65) Prior Publication Data
US 2005/0176658 A1    Aug. 11, 2005

Related U.S. Application Data

(60) Provisional application No. 60/517,612, filed on Nov. 4, 2003.

(51) Int. Cl.
*A61K 31/7056* (2006.01)
*A61K 31/551* (2006.01)
*A61N 5/00* (2006.01)
*A61P 35/00* (2006.01)

(52) U.S. Cl. ............... 514/320; 514/366; 514/250; 514/43; 514/220; 514/420; 600/1

(58) Field of Classification Search .......... 514/43, 514/420, 220, 320, 366, 25; 600/1
See application file for complete search history.

(56) References Cited

U.S. PATENT DOCUMENTS

2002/0150534 A1* 10/2002 Yu et al. .......... 424/1.49
2006/0088545 A1*  4/2006 Ensoli .............. 424/188.1

OTHER PUBLICATIONS

Bolen, "Liposarcomas a Histogenic Approach to the Classification of Adipose Tissue Neoplasms", American Journal of Sugical Pathology, 1984, 8, pp. 3-17.*
Brennan, M.F., et al. Soft tissue sarcoma. In: DeVita VT Jr., Hellman S, Rosenberg SA, eds. *Cancer: Principles & Practice of Oncology.* 6th ed. Philadelphia, PA: Lippincott-Raven Publishers, (2001).
Patel, S.R., et al. Myxoid liposarcoma: experience with chemotherapy. *Cancer* 74: 1265-1269 (1994).
Antman K, Crowley J, Balcerzak SP, Rivkin SE, Weiss GR, Elias A, Natale RB, Cooper RM, Barlogie B, Trump DL, Doroshow JH, Aisner J, Pugh RP, Weiss RB, Cooper BA, Clamond GH, and Baker LH. An Intergroup phase III randomized study of doxorubicin and dacarbazine with or without ifosfamide and mesna in advanced soft tissue and bone sarcomas. *J Clin Oncol* 11: 1276-1285, 1993.

Atherton, D. J.; Pitcher, D. W.; Wells, R. S.; MacDonald, D. M.: A syndrome of various cutaneous pigmented lesions, myxoid neurofibromata and atrial myxoma: the NAME syndrome. *Brit. J. Derm.* 103: 421-429, 1980.
Bernstein E, Caudy AA, Hammond SM, and Hannon GJ. Role for a bidentate ribonuclease in the initiation step of RNA interference. *Nature* 409: 363-366, 2001.
Borden EC, Baker LH, Bell RS, Bramwell V, Demetri GD, Eisenberg BL, Fletcher CDM, Fletcher JA, Ladanyi M, Meltzer P, O'Sullivan B, Parkinson DR, Pisters PWT, Saxman S, Singer S, Sundaram M, van Oosterom AT, Verweij J, Waalen J, Weiss SW, and Brennan MF. Soft tissue sarcomas of adults: state of the translational science. *Clin Cancer Res* 9: 1941-1956, 2003.
Caron M, Auclair M, Vigouroux C, Glorian M, Forest C, and Capeau J. The HIV protease inhibitor indinavir impairs sterol regulatory element-biding protein-1 intranuclear localization, inhibits preadipocyte differentiation, and induces insulin resistance. *Diabetes* 50: 1378, 2001.
Carr A, Samaras K, Chisholm DJ, and Cooper DA. Pathogenesis of HIV-1-protease inhibitor-associated peripheral lipodystrophy, hyperlipidaemia, and insulin resistance. *Lancet* 351: 1881-1883, 1998.
Carr A, Samaras K, Thorisdottir A, Kaufmann GR, Chisholm DJ, and Cooper DA. Diagnosis, prediction, and natural course of HIV-1 protease-inhibitor-associated lipodystrophy, hyperlipidemia, and diabetes mellitus. *Lancet* 353: 2093-2099, 1999.
Chow WA, and Doroshow JH. The Ewing's family of tumors (EFT) express the KIT and PDGFR-αtyrosine kinase receptors. *Proc Amer Assoc Cancer Res* 43: 1668, 2002.
Chow WA, Wilczynski SP, and Doroshow JH. Receptor tyrosine kinase inhibition in Ewing's family of tumors. *Proc Amer Assoc Cancer Res.* 44: 4700, 2003.
Coindre J-M, Terrier P, Guillou L, Le Doussal V, Collin F, Ranchère D, Sastre X, Vilain M-O, Bonichon F, and N'Guyen Bui B. Predictive value of grade for metastasis development in the main histologic types of adult soft tissue sarcomas: a study of 1240 patients from the French Federation of Cancer Centers Sarcoma Group. *Cancer* 91: 1914-1926, 2001.
Demetri GD, Fletcher CDM, Mueller E, Sarraf P, Naujoks R, Campbell N, Spiegelman BM, and Singer S. Induction of solid tumor differentiation by the peroxisome proliferator-activated receptor-γ ligand troglitazone in patients with liposarcoma. *Proc Natl Acad Sci USA* 96: 3951-3956, 1999.

(Continued)

*Primary Examiner*—Sreeni Padmanabhan
*Assistant Examiner*—Sahar Javanmard
(74) *Attorney, Agent, or Firm*—Perkins Coie LLP; Lauren Sliger (57) ABSTRACT

Liposarcomas are treated using HIV protease inhibitors, particularly nelfinavir. The protease inhibitors may be used alone or in combination with traditional cancer treatments, such as chemotherapy, radiotherapy, or surgery.

13 Claims, 4 Drawing Sheets

OTHER PUBLICATIONS

Dowell P, Flexner C, Kwiterovich PO, and Lane MD. Suppression of preadipocyte differentiation and promotion of adipocyte death by HIV protease inhibitors. *J Biol Chem* 52: 41325-41332, 2000.

Figgitt DP, and Plosker GL. Saquinavir soft-gel capsule: an updated review of its use in the management of HIV infection. *Drugs* 60: 481-516, 2000.

Flexner C. HIV-protease inhibitors. *N. Engl J Med* 338: 1281-1292, 1998.

Freireich EJ, Gehan EA, Rall DP, Schmidt LH, and Skipper HE. Quantitative comparison of toxicity of anticancer agents in mouse, rat, hamster, dog, monkey, and man. *Cancer Chemo Reports* 50: 219-244, 1966.

Gossen M, and Bujard H. Tight control of gene expression in mammalian cells by tetracycline-responsive promoters. *Proc. Natl. Acad. Sci. USA.* 89: 5547-5551, 1992.

Jemal A, Murray T, Samuels A, Ghafoor A, Ward E, and Thun MJ. Cancer statistics, 2003. *CA Cancer J Clin* 53: 5-26, 2003.

Kim JB, and Spiegelman BM. ADD1/SREBP1 promotes adipocyte differentiation and gene expression linked to fatty acid metabolism. *Genes & Dev* 10: 1096-1107, 1996.

Kim JB, Wright HM, Wright M, and Spiegelman BM. ADD1/SREBP1 activates PPARγ through the production of endogenous ligand. *Proc. Natl. Acad. Sci. USA.* 95: 4333-4337, 1998.

Koeffler HP. Peroxisome proliferator-activated receptor β and cancers. *Clin Cancer Res* 9: 1-9, 2003.

Lairmore, TC, Wells, SA, Jr., Moley, JF, Brennan MF, Cancer of the Endocrine System. In: DeVita VT Jr., Hellman S, Rosenberg SA, eds. Cancer: Principles & Practice of Oncology. 6th ed. Philadelphia, PA: Lippincott-Raven Publishers: Chapter 38, pp. 1727-1891, 2001.

Le Grice SFJ, Mills J, and Mous J. Active site mutagenesis of the AIDS virus protease and its alleviation by trans complementation. *EMBO J* 7: 2547-2553, 1988.

McCune JM, Namikawa R, Kaneshima H, Shultz LD, Lieberman M, and Weissman IL. The SCID-hu mouse: murine model for the analysis of human hematolymphoid differentiation and function. *Science* 241: 1632-1639, 1988.

*Mendelian Inheritance in Man* (OMIN), http://www.ncbi.nlm.nih.gov/, OMIN reference No. 151900. no date available.

*Mendelian Inheritance in Man* (OMIN), http://www.ncbi.nlm.nih.gov/, OMIN reference No. 160980. no date available.

Palella FJ, Delaney KM, Moorman AC, Loveless MO, Fuhrer J, Satten GA, Aschman DJ, Holmberg SD, and the HIV Outpatient Study Investigators. Declining morbidity and mortality among patients with advanced human immunodeficiency virus infection. *N Engl J Med* 338: 853-860, 1998.

Riddle TM, Kuhel DG, Woollett LA, Fichtenbaum CJ, and Hui DY. HIV protease inhibitor induces fatty acid and sterol biosynthesis in liver and adipose tissues due to accumulation of activated sterol regulatory element-binding proteins in the nucleus. *J Biol Chem* 276: 37514-37519, 2001.

Shetty BV, Kosa MB, Khalil DA, and Webber S. Preclinical pharmacokinetics and distribution to tissue of AG1343, an inhibitor of human immunodeficiency virus type I protease. *Antimicrob Agents Chemo* 40: 110-114, 1996.

Shih, C-C, Hu J, Arber D, LeBon T, and Forman SJ. Transplantation and growth characteristics of human fetal lymph node in immunodeficient mice. *Exp Hematol* 28: 1046-1053, 2000.

Shih, CC, Hu MCT, Hu J, Medeiros J, and Forman SJ. Long-term Ex vivo maintenance and expansion of transplantable human hematopoietic stem cells. *Blood* 94: 1623-1636, 1999.

Shih, CC, Weng Y, Mamelak A, LeBon T, Hu MCT, and Forman SJ. Identification of a candidate human neurohematopoietic stem-cell population. *Blood* 98: 2412-2422, 2001.

Sreekantaiah C, Ladanyi M, Rodriguez E, and Chaganti RS. Chromosomal aberrations in soft tissue tumors. Relevance to diagnosis, classification, and molecular mechanisms. *Am J Pathol* 144: 1121-1134, 1994.

Tallman MS, Andersen JW, Schiffer CA, Appelbaum FR Feusner JH, Ogden A, Shepherd L, Willman C, Bloomfield CD, Rowe JM, and Wiernik PH. All-*trans*-retinoic acid in acute promyelocytic leukemia. *N Engl J Med* 337: 1021-1028, 1997.

Tontonoz P, Hu, E, and Spiegelman BM. Stimulation of adipogenesis in fibroblasts by PPARγ2, a lipid-activated transcription factor. *Cell* 79: 1147-1156, 1994.

Tontonoz P, Singer S, Forman BM, Sarraf P, Fletcher JA, Fletcher CDM, Brun RP, Mueller E, Altiok S, Oppenheim H, Evans RM, and Spiegelman BM. Terminal differentiation of human liposarcoma cells induced by ligands for peroxisome proliferator-activated receptor γ and the retinoid X receptor. *Proc. Natl. Acad. Sci. USA.* 94: 237-241, 1997.

Warrell RP, Frankel SR, Miller WH, Scheinberg DA, Itri LM, Hittelman WN, Vyas R, Andreeff M, Tafuri A, Jakubowski A, Gabrilove J, Gordon MS, and Dmitrovsky E. Differentiation therapy of acute promyelocytic leukemia with tretinoin (all-*trans*-retinoic acid). *N Engl J Med* 324: 1385-1393, 1992.

Zhang B, Macnaul K, Szalkowski D, Li Z, Berger J, and Moller DE. Inhibition of adipocyte differentiation by HIV protease inhibitors. *J Clin Endocr Metab* 84: 4274-4277, 1999.

\* cited by examiner

METHOD OF USING PROTEASE INHIBITORS FOR THE TREATMENT OF LIPOSARCOMAS

PRIORITY CLAIM

This application claims priority to U.S. Provisional Application Ser. No. 60/517,612, filed Nov. 4, 2003, which is incorporated herein by reference in its entirety, including drawings.

FIELD OF THE INVENTION

The present invention relates to the field of treating soft tissue and fat-related tumors. Specifically, the invention is directed toward the treatment of liposarcomas.

BACKGROUND OF THE INVENTION

Each of the references cited herein is incorporated by reference in its entirety. A complete listing of the citations is set forth at the end of the specification.

Adult soft tissue sarcomas constitute a family of relatively uncommon tumors. They account for approximately 1% of the cancer diagnoses each year in the United States (1). Sarcomas consist of a heterogeneous group of histologically distinct malignancies that arise from mesenchymal tissues. Liposarcomas are, for example, malignant tumors derived from primitive or embryonal lipoblastic cells and are histologically distinct from Kaposi's sarcoma, an indolent vascular tumor.

Liposarcomas are the second most common adult soft tissue sarcoma, accounting for approximately 20% of all sarcomas. They range from low-grade, well-differentiated, and myxoid liposarcomas to high-grade, round cell, and pleomorphic liposarcomas (2). Well-differentiated liposarcomas can exhibit aggressive local invasion but rarely metastasize until late in their course when they progress to high-grade undifferentiated sarcomas of other histologic origin (i.e., leiomyosarcoma, rhabdomyosarcoma, or even osteosarcoma). Round cell and pleomorphic liposarcomas have a high potential for distant metastasis and survival rates are poor, with 5-year survival of 20-30% in patients with these tumors (3). Liposarcomas may also be a feature of other conditions including but not limited to Type 1 Carney Complex (30, 31) or multiple lipomatosis (31). Most clinical trials of chemotherapy for advanced soft tissue sarcomas do not differentiate liposarcomas from other soft tissue sarcomas. Single-agent doxorubicin chemotherapy for advanced soft tissue sarcomas yields a modest response rate of about 25% (3). Doxorubicin in combination with ifosfamide typically induces responses of 20-40% in less-differentiated tumors. Unfortunately, in a large U.S. cooperative group study of the combination of doxorubicin, ifosfamide, and dacarbazine for advanced soft tissue sarcomas, the response rate of 32% was only modestly better than the response rate for doxorubicin and dacarbazine alone (17%) (29). The median time to progression was modestly improved from 4 to 6 months. Severe and life-threatening toxicities were more common, however (55% vs. 88%) (29).

Surgery, alone or in combination with chemotherapy and/or radiotherapy, remains the primary treatment modality for liposarcomas. Metastatic liposarcoma is associated with an extremely poor prognosis, with average 5-year survivals ranging from 70% to as low as 25% depending on the type of tumor. Conventional chemotherapy for recurrent liposarcomas or for metastatic liposarcoma leads to a complete response in only about 10% of patients, and thus, is largely palliative (4, 5). Novel, targeted, and less toxic therapies are urgently needed.

Induction of terminal differentiation represents one approach in the search for novel targeted therapeutic agents for certain malignancies. For example, the nuclear retinoic acid receptor α (RARα), which plays an important role in the differentiation and malignant transformation of cells of the myelocytic lineage, is a target for intervention in acute promyelocytic leukemia (APL) (6). Differentiation therapy with all-trans retinoic acid has become the standard of care for this disease (7).

Similar to RARα in APL, the nuclear receptor peroxisome proliferator-activated receptor γ (PPARγ) and the retinoid X receptor α (RXRα) form a heterodimeric complex that functions as a central regulator of adipocyte differentiation. Primary human liposarcoma cells express high levels of PPARγ and can be induced to undergo terminal differentiation by treatment with PPARγ ligands such as the antidiabetic medication, pioglitazone (a 2,4-thiazolidinedione) (8).

A clinical trial of a different thiazolidinedione, troglitazone, was conducted for treatment of patients with intermediate to high-grade liposarcoma (9). Biopsies of tumors treated with troglitazone demonstrated evidence of differentiation and reduction of cellular proliferation. Although the long-term effect of thiazolidinediones on liposarcomas requires further study, the toxicity of therapy was negligible, and one patient exhibited temporary disease stabilization. These studies demonstrate that targeted therapy for solid tumors such as liposarcomas is viable.

The development of highly active antiretroviral therapy (HAART) has significantly improved the outcome of individuals infected with human immunodeficiency virus (HIV) type-1 infection (10). An integral component of HAART is the HIV protease inhibitor. The HIV protease enzyme targets the amino acid sequences in the gag and gag-pol polyproteins, which must be cleaved before nascent viral particles (virions) can mature (11). Proviral DNA lacking functional protease produces immature, noninfectious viral particles (12). HIV protease inhibitors prevent cleavage of gag and gag-pol protein precursors in acutely and chronically infected cells, arresting maturation and thereby blocking the infectivity of nascent virions (11). Four HIV protease inhibitors, indinavir, nelfinavir, ritonavir, and saquinavir, are structurally related, but differ based upon the amino acid sequences recognized and cleaved in HIV proteins (11).

An unanticipated consequence of HAART has been the development of a distinct clinical syndrome consisting of peripheral lipoatrophy and central fat accumulation associated with insulin resistance and hyperlipidemia, which is directly linked to the use of the HIV protease inhibitor (13). This clinical syndrome is labeled "HIV protease-induced lipodystrophy syndrome" (14). The pathophysiology of HIV protease-induced lipodystrophy syndrome is currently under intense investigation and debate.

One mechanism proposed to explain the pathophysiology of the syndrome is the inhibition of adipocyte differentiation via inhibition of PPARγ (15). Another theory is the alteration in the level of sterol regulatory element binding protein 1 (SREBP-1) (16-18). SREBP-1 is a member of the basic helix-loop-helix-leucine zipper transcription factor family (19). It promotes lipogenic gene expression (19) and stimulates production of an unidentified PPARγ ligand (20). Thus, SREBP-1 and PPARγ cooperatively promote adipogenesis and subsequent maintenance of the adipocyte phenotype. Consistent with this hypothesis, HIV protease inhibitors have been shown to induce lipolysis by reducing levels of SREBP-1 (21). Further, this property of HIV protease inhibitors seems to target differentiated adipocytes selectively. It has been demonstrated that incubation with ritonavir, saquinavir and nelfinavir for 48 hours induced apoptosis in differentiated adipocytes, but not in pre-adipocytes (21).

Proteases are important components in the replication of a number of viruses and viral protease inhibitors represent a growing class of anti-viral therapeutics. A number of HIV protease inhibitors are currently in the clinic, and protease inhibitors for additional viruses are under investigation.

Thus, there is a serious need for improvement of treatment methods for liposarcoma patients. If lipodystrophy were observed with the clinical use of a protease inhibitor, then the findings would indicate that such a protease inhibitor may also be useful for the treatment of liposarcoma. The present invention addresses this need with novel methods of use of inhibitors of viral proteases.

SUMMARY OF THE INVENTION

A first aspect of the present invention comprises the use of inhibitors of viral proteases for liposarcoma therapy. Preferably, liposarcoma-specific growth inhibition is achieved using the HIV protease inhibitor, nelfinavir. Nelfinavir potently and selectively inhibits liposarcoma clonogenicity at concentrations that are clinically relevant for HIV protease inhibition.

A second aspect of the present invention provides the mechanism of nelfinavir-mediated liposarcoma growth inhibition in vitro and in vivo in the severe combined immunodeficient-human (SCID-hu) murine model.

Another aspect of the present invention uses a tetracycline-regulated system to control expression of antisense RNA to SREBP-1 and/or PPARγ to study nelfinavir-mediated inhibition of liposarcoma clonogenicity. SREBP-1 regulates lipid synthesis and is expressed primarily in adipose cells. Other methods of selectively inhibiting gene expression or gene products such as the use of small interfering RNAs (siRNAs) are contemplated.

These and other aspects are elucidated further in the following detailed description. While there may be many methods of action of any drug, our invention is not limited to any mode of action or hypothetical/proposed mode of action. The examples are intended only to illustrate the invention, and are not meant as limitations on it.

DETAILED DESCRIPTION

Definitions

"Clonogenic assay" means in vitro culturing of neoplastic cells to test their radiosensitivity or chemosensitivity and probable clinical assay of a therapeutic agent.

A "pharmaceutically effective dose" or "therapeutically effective amount" is an amount of a viral protease inhibitor, such as nelfinavir, that produces a desired therapeutic effect. In this case, the desired therapeutic effect is the treatment of liposarcomas. The precise amount of the pharmaceutically effective dose of a viral protease inhibitor is one that will yield the most effective results in terms of efficacy of treatment in a given subject (also known as a "patient") will depend upon the activity, pharmacokinetics, pharmacodynamics, physiological condition of the subject (including age, sex, disease type and stage, general physical condition, responsiveness to a given dosage and type of medication), the nature of pharmaceutically acceptable carrier in a formulation, and a route of administration, among other potential factors. Those skilled in the clinical and pharmacological arts will be able to determine these factors through routine experimentation consisting of monitoring the subject and adjusting the dosage. Remington: The Science and Practice of Pharmacy (Gennaro ed. 20$^{th}$ edition, Williams & Wilkins Pa., USA) (2000).

Dosage of the particular protease inhibitor administered will depend on factors, such as the pharmacodynamic characteristics of the protease inhibitor, the mode and route of administration, and the whether the protease inhibitor is being administered alone or in combination with other therapeutics. The age, health, weight, progression of the disease, types of symptoms and other individual factors relating to the subject being treated will be evaluated by a skilled clinician, who can adjust the dose based upon these factors. A daily dosage of the protease inhibitor can be expected to be about 0.001 to about 1000 milligrams per kilogram of body weight, with the preferred dose being about 0.05 to about 100 mg/kg and the more preferred dose being about 0.1 to about 40 mg/kg. Dosages may also be adjusted based on in vitro or animal dosages, showing effective molar concentrations for a given protease inhibitor and then calculating the dosage for a human subject based on the factors listed above and other physiological and metabolic conversation factors.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a viral protease inhibitor from one tissue, organ, or portion of the body, to another tissue, organ, or portion of the body. Each component must be "pharmaceutically acceptable" in the sense of being compatible with the other ingredients of the formulation. It must also be suitable for use in contact with the tissue or organ of humans and animals without excessive toxicity, irritation, allergic response, immunogenecity, or other problems or complications, commensurate with a reasonable benefit/risk ratio.

Pharmaceutically acceptable carriers for the viral protease inhibitors are generally known in the art because of their current use in treating patients with HIV. Briefly, the compositions comprising viral protease inhibitors may include sugars, starches, cellulose, powdered tragacanth, malt, gelatin, talc, excipients, oils, glycols, esters, buffering agents, and other non-toxic compatible substances employed in pharmaceutical formulations.

Formulations suitable for oral administration may be in the form of capsules, cachets, pills, tablets, lozenges, powders, as granules or a paste, as a solution or a suspension in an aqueous or non-aqueous liquid, as an oil-in-water or water-in-oil liquid emulsion, as an elixir or syrup, or as pastilles (using an inert base, such as gelatin and glycerin, or sucrose and acacia), each containing a predetermined amount of a viral protease inhibitor as an active ingredient. In addition, the liquid dosage forms may contain inert diluents commonly used in the art.

Formulations for the topical or transdermal administration of an HIV protease inhibitor include powders, sprays, ointments, pastes, creams, lotions, gels, solutions, patches and inhalants. The active component may be mixed under sterile conditions with a pharmaceutically acceptable carrier, and with any preservatives, buffers, or propellants that may be required.

A "route of administration" for an HIV protease inhibitor can be by any pathway known in the art, including without limitation, oral, enteral, nasal, topical, rectal, vaginal, aerosol, transmucosal, transdermal, ophthalmic, pulmonary, and/or parenteral administration. A parenteral administration refers to an administration route that typically relates to injection. Parenteral administration includes, but is not limited to, intravenous, intramuscular, intraarterial, intraathecal, intracapsular, infraorbital, intracardiac, intradermal, intraperitoneal, transtracheal, subcutaneous, subcuticular, intraarticular, subcapsular, subarachnoid, intraspinal, via intrastemal injection, and/or via infusion.

"Treatment" of or "treating" a liposarcoma may mean preventing the liposarcoma by causing clinical symptoms not to develop, inhibiting the liposarcoma by stopping or reducing the symptoms, the development of the liposarcoma, and/or slowing the rate of development of the liposarcoma, relieving the liposarcoma by causing a complete or partial regression of the liposarcoma, reducing the risk of developing the liposarcoma, or a combination thereof.

"Radiotherapeutic agents" or "chemotherapeutic agents" mean any chemical compound or treatment method that induces cell damage and/or results in cell death. Such agents include azathioprine, BCG, androgens, asparagine, bleomycin, epirubicin, gemcitabine, hydroxyurea, interferon alpha, beta or gamma, 6-mercaptopurine, paclitaxel, thioguanine, adriamycin, 5-fluorouracil, etoposide, camptothecin, actinomycin-D, mitomycin C, cisplatin, or other drugs. The agents may also include radiation and waves like gamma radiation, X-rays, UV-irradiation, microwaves, and electroemissions. Other chemotherapeutic substances may include natural or synthetic antibodies, metastases-inhibiting compounds, growth factor inhibitors, oncogenic protein inhibitors, such as for inhibiting RAS, protein kinase inhibitors, or DNA topoisomerase inhibitors.

Aspects

One aspect of the present invention involves using one or more small molecule HIV protease inhibitors to inhibit liposarcoma formation and/or growth. Nelfinavir is the preferred HIV protease inhibitor, although ritonavir may also be used if administered at doses of 10 µM or greater. Nelfinavir typically inhibits in a dose-dependent fashion. These HIV protease inhibitors may be administered separately or together as part of a therapeutic strategy. Preferably, HIV protease inhibitor is administered in a pharmaceutically acceptable carrier. Pharmaceutically acceptable carriers are known in the art because of the use for HIV protease inhibitors for standard HIV treatment.

The usual route of administration for HIV protease inhibitors is oral, although other routes such as parenteral administration may be used. In light of the solid form of the liposarcomas, the preferred route of administration for the inhibitors of the present invention is by direct injection or infusion to the site of the tumor. The HIV protease inhibitor should be administered in a therapeutically effective amount and over a course of time so that the liposarcoma tumor is treated.

The HIV protease inhibitor, administered alone or in combination, may also be used in conjunction with other types of known therapies for treating cancers, such as other chemotherapy or radiotherapy. The inhibitor may be administered at any time from before the removal of the liposarcoma to after the surgical removal of the liposarcoma. The HIV protease inhibitor may even be administered prophylactically to a person at high risk of developing a liposarcoma.

Another aspect of the present invention relates to the use of severe combined immunodeficient-human (SCID-hu) mice for examining the mechanism of nelfinavir-mediated liposarcoma growth inhibition in vitro and in vivo. The mice can be used to test variations of methods of the present invention, including optimizing the dose of nelfinavir to be administered based on the given route of administration.

A further aspect of the present invention relates to a tetracycline-regulated system to control expression of antisense RNA to SREBP-1 and/or PPARγ to study nelfinavir-mediated inhibition of liposarcoma clonogenicity. SREBP-1 and/or PPARγ genes may also be controlled by siRNAs.

Experiments

1. Nelfinavir Inhibits Human SW872 Liposarcoma Clonogenicity

To determine whether HIV protease inhibitors inhibit liposarcoma clonogenicity, SW872 cells (high-grade liposarcoma from a 36 year-old male Caucasian) from the American Type Culture Collection (ATCC, Manassas, Va.) were treated for 4 hours with increasing concentrations of the HIV protease inhibitors: indinavir, ritonavir, saquinavir and nelfinavir (NIH AIDS Research & Reference Reagent Program, Rockville, Md.). The maximum plasma concentration ($C_{max}$) for these drugs in humans at the recommended dose and regimen are: indinavir (12.54 µM), nelfinavir (6.97 µM), ritonavir (15.53 µM), and saquinavir (3.67 µM) (11, 22). The experimental conditions were intended to bracket these clinically relevant concentrations.

Figure 1:
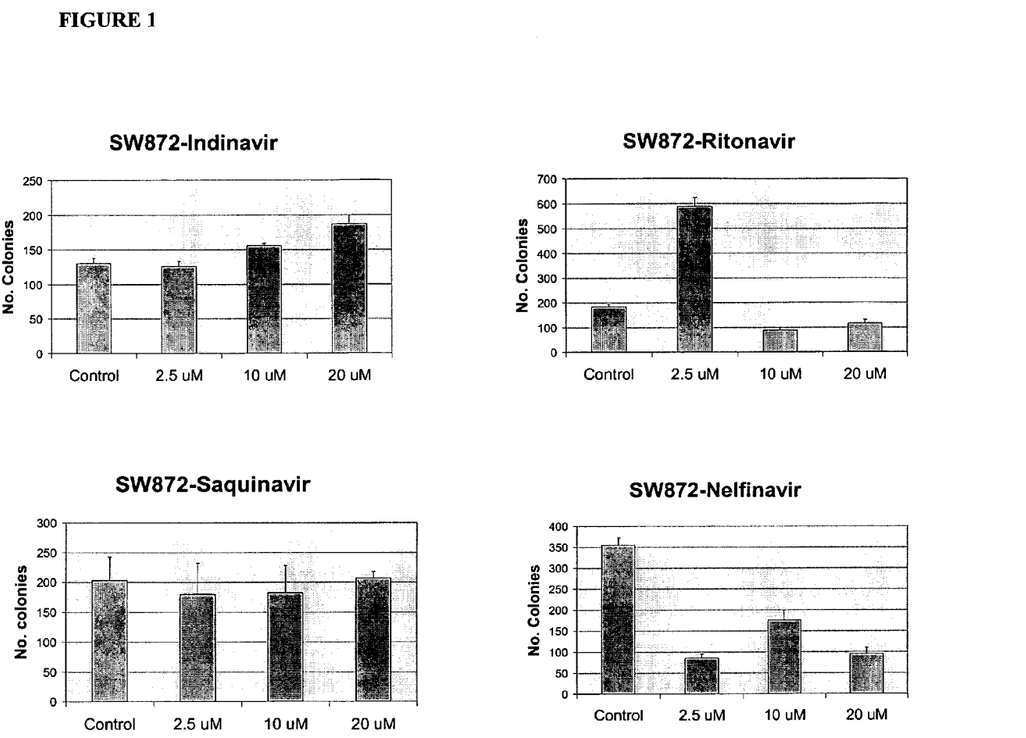
FIG. 1 contains four bar graphs that each shows the effect of a different HIV protease inhibitor (indinavir, ritonavir, saquinavir, and nelfinavir) on colony formation of SW872 cells at varying concentrations. A control is also shown in each instance, representing only SW872 liposarcoma cells without the addition of the relevant HIV protease inhibitor.

Two thousand treated cells were plated into 60 mm tissue culture plates in triplicate, and colonies ($\geq$40 cells/colony) were scored at 7-10 days with the Eagle Eye II gel documentation system (Stratagene, La Jolla, Calif.). FIG. 1 summarizes the mean and standard deviation of the triplicate colony counts for each experimental condition. The results demonstrate that nelfinavir inhibits SW872 liposarcoma clonogenicity at clinically relevant concentrations as low as 2.5 µM. The other HIV protease inhibitors exhibit varying behavior. Ritonavir inhibits colony growth if administered in a concentration of at least 10 µM.

2. Nelfinavir Selectively Inhibits SW872 Liposarcoma Clonogenicity.

To determine whether nelfinavir selectively inhibits SW872 liposarcoma clonogenicity, human 293 embryonic kidney cells (ATCC), human HT1080 fibrosarcoma cells (ATCC), and SW872 cells were treated with nelfinavir at the same experimental concentrations as in the first experiment.

Figure 2:
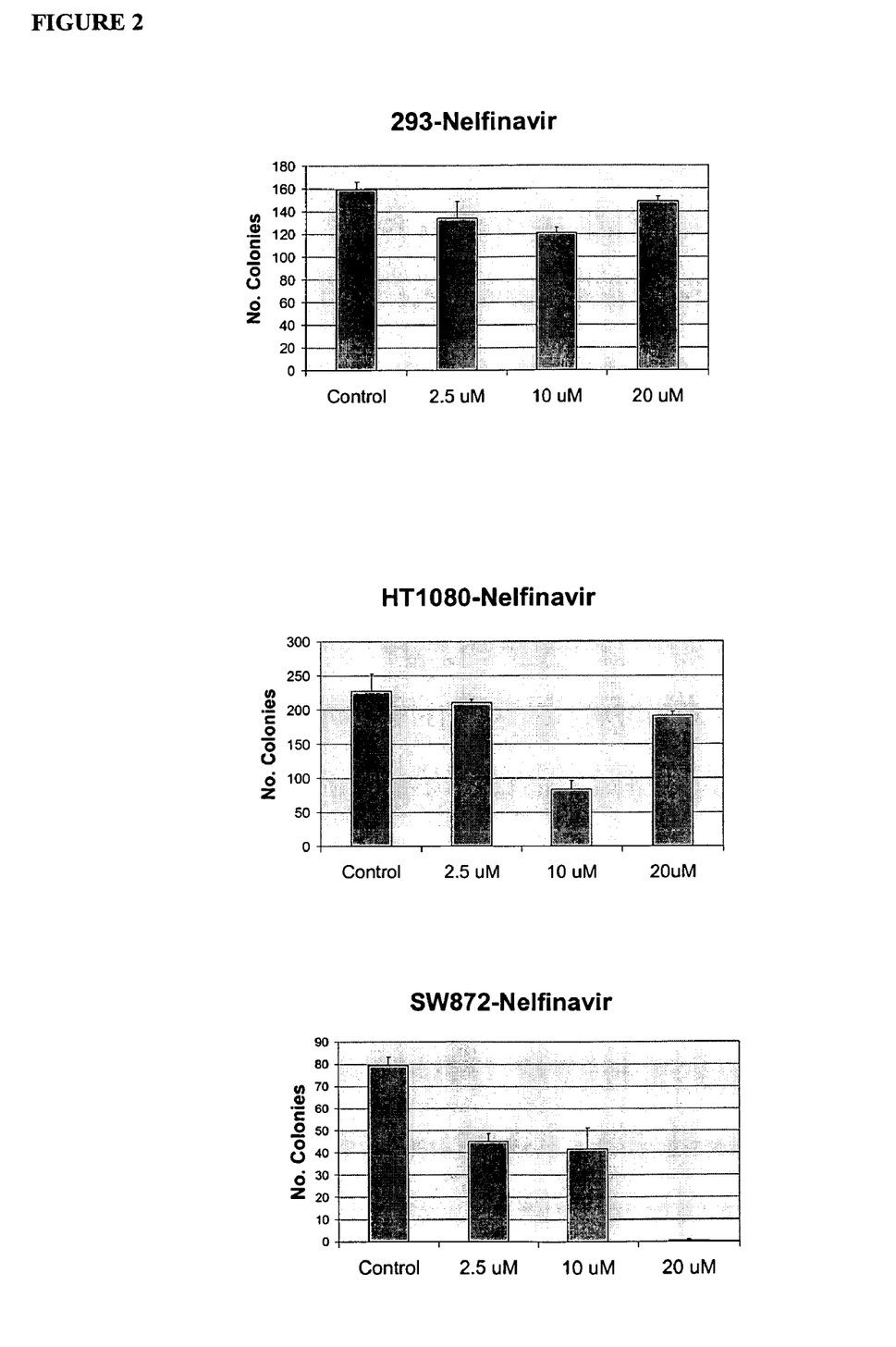
FIG. 2 contains three bar graphs showing colony formation in the presence of varying concentrations of nelfinavir as applied to three types of cell lines, SW872 liposarcoma cells, human 293 embryonic kidney cells (ATCC), and human HT1080 fibrosarcoma cells (ATCC).

One thousand treated cells were plated in triplicate in this instance, and colonies were similarly scored. The mean and standard deviation for each experimental condition are reported in FIG. 2. The data clearly indicates that only the liposarcoma cell line is affected by increasing concentrations of nelfinavir.

These results show that nelfinavir selectively inhibits liposarcoma clonogenicity, while minimally affecting embryonic kidney and fibrosarcoma clonogenicity. The marked reduction in colonies in the SW872 cell line for nelfinavir (20 µM) in this experiment compared to the preliminary experiment reported in FIG. 1 may have resulted from a reduction in the number of cells plated from 2000 to 1000. Only 1000 cells were plated in the second experiment set after discovering how many colonies resulted when 2000 cells were plated.

3. Nelfinavir Inhibits Human S2 Liposarcoma Clonogenicity

Figure 3:
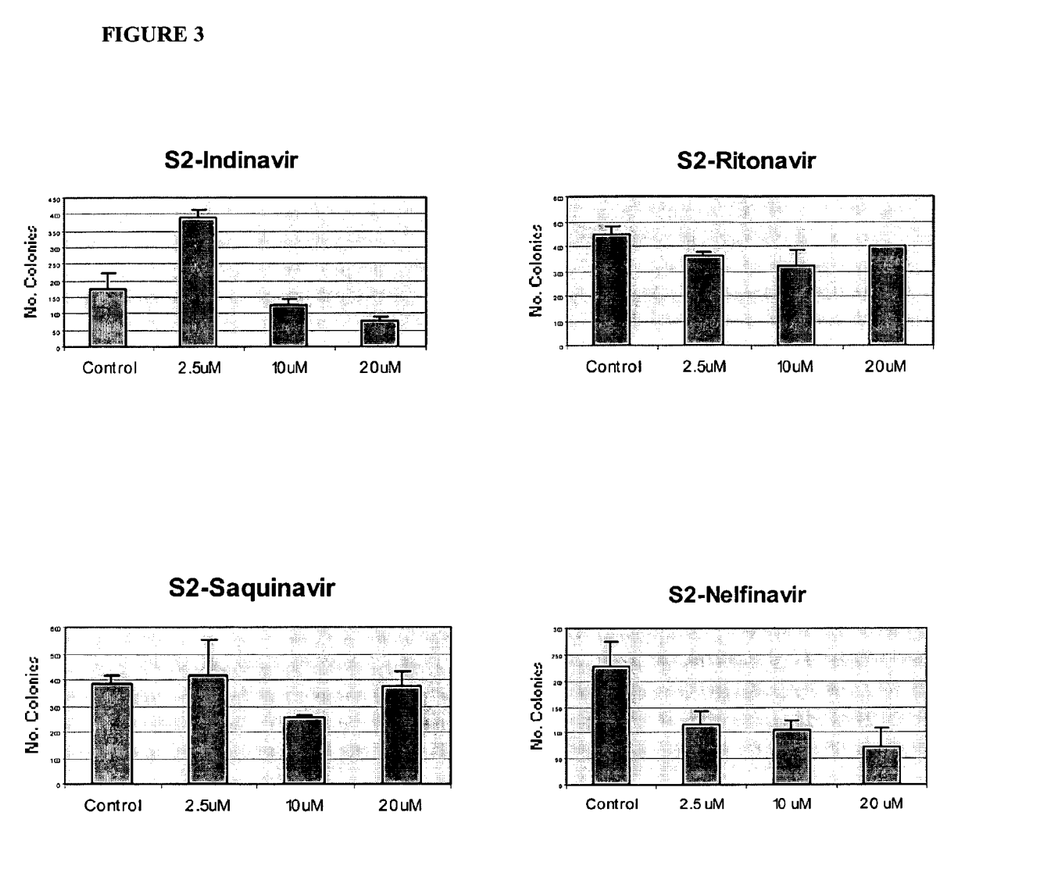
FIG. 3 comprises four bar graphs that each demonstrates the effect of a different HIV protease inhibitor (indinavir, ritonavir, saquinavir, and nelfinavir) on colony formation of S2 high-grade liposarcoma cells at concentrations of 2.5 µM, 10 µM, and 20 µM. A control is also shown in each instance, representing only S2 cells without the addition of the relevant HIV protease inhibitor.

A second high-grade liposarcoma cell line, S2 (a kind gift from Dr. Wei Wen, City of Hope Medical Center), was tested for protease inhibitor (PI) therapy for liposarcoma. The purpose of the experiment was to determine whether nelfinavir-mediated inhibition of liposarcoma clonogenicity could be reproduced in S2 cells. As with the SW872 experiment, S2 cells with nelfinavir, indinavir, ritonavir, and saquinavir. Two thousand cells were treated for four hours with the concentrations of zero (control), 2.5 µM, 10 µM, and 20 µM of each PI as indicated in FIG. 3, and plated into 60 mm tissue culture plates in triplicate. Colonies (≧40 cells/colony) were scored at 7-10 days with the Eagle Eye II gel documentation system (Stratagene, La Jolla, Calif.). FIG. 3 summarizes the mean and standard deviation of the triplicate colony counts for each experimental condition. The results demonstrate that nelfinavir inhibits clonogenicity in the S2 liposarcoma cell line similar to that observed in the SW872 cell line, and thus, corroborate the findings of the present invention.

4. Nelfinavir Upregulates SREBP-1 Protein Levels in S2 Cells.

Figure 4:
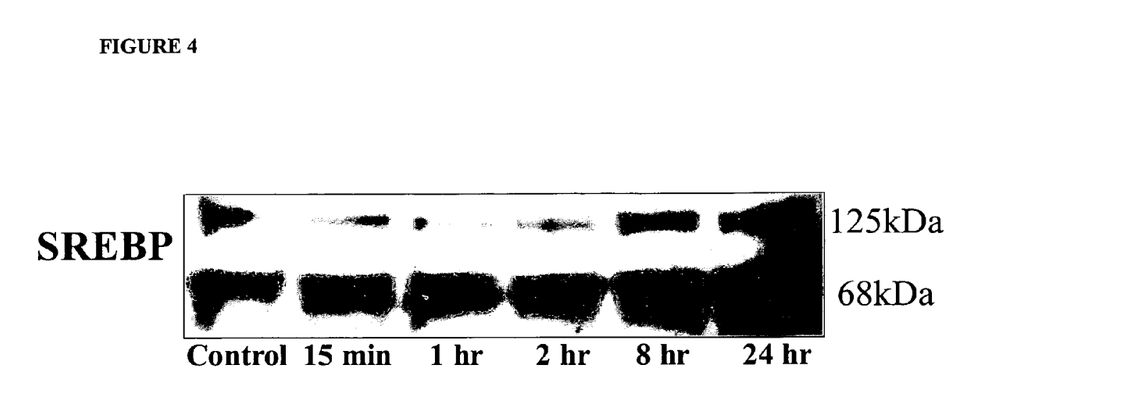
FIG. 4 is an image of S2 cells treated with 10 µM of nelfinavir at the indicated time points and Western blotted for detection of SREBP-1.

To determine whether nelfinavir upregulates expression of SREBP-1 in S2 cells similar to that observed in SW872 cells, S2 cells were treated with 10 µM of nelfinavir for the indicated time periods, and western blotting for detection of SREBP-1 protein was performed with a rabbit polyclonal antibody (H-160, Santa Cruz Biotechnology, Inc., Santa Cruz, Calif.). SREBP-1 is produced as an inactive 125 kDa, membrane-bound transcription factor. In order to influence transcription, the $NH_2$-terminal domain of SREBP-1 must be proteolytically released from the membrane to enter the nucleus (68 kDa). Similar to that observed for SW872, nuclear active, and to a significantly lesser extent, precursor forms of SREBP-1 were upregulated in a time-dependent fashion. See FIG. 4. These experiments show that nelfinavir upregulates expression of SREBP-1 in both of the high-grade liposarcoma cell lines tested. The experiments further demonstrate that nelfinavir preferentially upregulates expression of SREBP-1 in tumors that develop from adipose tissue.

5. Primary Solid Tumors Grow in a Severe Combined Immunodeficient-Human (SCID-Hu) Murine Model.

The SCID-hu murine model is created by xenotransplantation of human tissues into the severe combined immunodeficient C.B-17 scid/scid (SCID) mouse (23). The SCID-hu mouse is a more efficient model than a nude mouse to establish primary human tumors. Hsd:RH-mu athymic nude mice contain a dysfunctional, rudimentary thymus that may give rise to residual T-cells that could reject xenografted tissue, whereas homozygous SCID-hu mice are unable to mount an effective cellular or humoral immune response to foreign antigen because of a defective recombinase function, which leads to unproductive antigen receptor gene rearrangement in both T and B cells (24). The present inventors have successfully xenografted and expanded primary human colon, lung, bladder, ovarian, and Merkel cell carcinomas, as well as melanomas, lymphomas, and fibrosarcoma.

6. Molecular Mechanism of the Selective Inhibition of SW872 Liposarcoma Clonogenicity by Nelfinavir.

A. Western Blot Analysis of SREBP-1 and PPARγ Protein Levels After Nelfinavir Exposure.

Alterations in both SREBP-1 and PPARγ levels have been proposed as the mechanisms underlying of HIV protease-induced lipodystrophy (15-18, 21). To determine whether a similar mechanism is responsible for the observation of nelfinavir-mediated inhibition of liposarcoma clonogenicity, whole cell extracts are prepared from control and nelfinavir-treated SW872 cells for SDS-PAGE electrophoresis. After transfer to polyvinylidene fluoride membranes, the extracts are probed with rabbit polyclonal antibodies to SREBP-1 and PPARγ (Santa Cruz Biotechnology, Santa Cruz, Calif.). Protein detection is performed by ECL using commercially available reagents as per the manufacturer's instructions (Applied Biosystems, Foster City, Calif.). To control for protein-loading, the membranes are stripped and reprobed with antibody to β-actin (Santa Cruz Biotechnology).

293 and HT1080 cell lines are relatively resistant to nelfinavir-mediated inhibition of clonogenicity because they possess low levels of endogenous SREBP-1 and/or PPARγ levels. Western blot analysis is performed similarly in these untreated cell lines. Alternatively, endogenous levels of SREBP-1 and/or PPARγ in these cell lines are similar to SW872 cells, but are relatively resistant to nelfinavir-mediated effects. In this instance, nelfinavir exposure should not alter the levels of SREBP-1 and/or PPARγ. Protein levels of SREBP-1 and/or PPARγ are analyzed by Western blot in nelfinavir-treated 293 and HT1080 cells.

B. Establishment of Stable SREBP-1 and PPARγ-Overexpressing Heterologous Cell Lines.

After confirmation by Western blot analysis, stable SREBP-1 and PPARγ-overexpressing heterologous cell lines are established. Others have previously demonstrated that expression of PPARγ in NIH 3T3 cells was undetectable, however when overexpressed in these cells, PPARγ promoted adipose differentiation of these NIH 3T3 cells under conditions permissive for adipogenesis (25). The present experiment obtains this heterologous cell line, and performs clonogenic assays and Western blot analysis of PPARγ levels after exposure to nelfinavir.

Nelfinavir should not alter clonogenicity of the parental NIH 3T3 cells, whereas it should reduce the clonogenicity of the PPARγ overexpressing cell line. The established cell line is used rather than creating PPARγ-overexpressing 293 and HT1080 cell lines. Alternatively, SREBP-1 is responsible for the observed nelfinavir effect and an SREBP-1 overexpressing NIH 3T3 cell line is also established. This heterologous cell line may similarly develop adipogenic features such as accumulation cytoplasmic, triacylglycerol-rich lipid droplets under conditions permissive for adipogenesis (10% fetal calf serum, 5 µg/ml insulin, 0.5 mM methylisobutylxanthine, and 1 µM dexamethasone) (25). cDNA encoding SREBP-1 (ATCC) is then cloned into the pLP-CMVneo mammalian expression vector (BD Biosciences Clontech, Palo Alto, Calif.). Using an activated-dendrimer transfection reagent (SuperFect©, Qiagen, Valencia, Calif.), the pLP-CMVneo plasmid containing SREBP-1 are transfected into NIH 3T3 cells. After selection in G418, neomycin-resistant clones are identified and isolated.

To confirm functional expression of SREBP-1, adipogenesis is confirmed in the neomycin-resistant clones. The cells are stained with the lipophilic dye Oil Red O to confirm the presence of triacylglycerol accumulation as a marker of adipogenesis (25). This heterologous SREBP-1 cell line is then treated with nelfinavir, and clonogenic assays and Western blot analysis of SREBP-1 levels are then performed.

C. Establishment of a Regulated Antisense SREBP-1 and PPARγ System in SW872 Cells.

The present invention discovered that nelfinavir inhibits liposarcoma clonogenicity via reduction of SREBP-1 and/or PPARγ levels. Consequently, inhibition of clonogenicity by reducing levels of SREBP-1 and/or PPARγ in a nelfinavir-free system supports the hypothesis that nelfinavir inhibits clonogenicity in this fashion. Unfortunately, reduced levels of endogenous SREBP-1 and PPARγ are unlikely to be compatible with cell survival in adipogenic tumors. To circumvent this problem, a tetracycline regulated system is utilized to control expression of antisense RNA to SREBP-1 and/or PPARγ (26).

In the BD™ Tet-On System, a chimeric transactivator binds to the Tet Response Element (TRE) and activates transcription of the gene of interest in the presence of doxycycline (BD Biosciences Clontech). cDNA encoding SREBP-1 and PPARγ is cloned into the pTRE-Tight-EGFP Vector (BD Biosciences Clontech) in an antisense orientation, which places the antisense cDNA under the control of a minimal CMV promoter, which is regulated by the TRE. In addition, the vector allows selection for green fluorescent protein expression (GFP). The resulting plasmid is transfected stably into Tet 293 and HT1080 cell lines, which stably express the chimeric transactivator (BD Biosciences Clontech). GFP-positive clones are isolated by fluorescence-activated flow cytometry and expanded. The resulting clones are assayed for clonogenicity in the presence (antisense RNA production stimulated) and absence (antisense RNA production inhibited) of doxycycline.5. Nelfinavir-mediated inhibition of SW872 clonogenicity is reproducible in other liposarcoma cell lines.

To determine whether SW872 liposarcoma-specific inhibition of clonogenicity with nelfinavir is reproducible in other liposarcoma cell lines, the tests are also performed on other liposarcoma cell lines. These cell lines include the WLS-160 (Dr. Y Hirshaut, Laboratory of Immunodiagnosis, Memorial Sloan-Kettering Cancer Center, New York, N.Y.) and S. Ba (Dr. E. Boven, Department of Medical Oncology, Academic Hospital Vrije Universiteit, Amsterdam, The Netherlands). These cell lines are treated with nelfinavir at the same concentrations as used in earlier experiments, and clonogenicity is determined.

7. Toxicities and Maximally Tolerated Dose (MTD) of Nelfinavir in the Severe Combined Immunodeficient-Human (SCID-hu) Murine Model.

Nelfinavir is commercially available in an oral powder for pediatric patients (50 mg/g, Agouron Pharmaceuticals, La Jolla, Calif.). A $C_{max}$ of 6.97 μM (4 mg/L) for nelfinavir is reached after 750 mg oral 3 times daily or 1250 mg oral twice daily in patients with HIV infection (11). The oral bioavailability of nelfinavir is 70-80% when administered with food in humans (11), but is lower in fed rats (43%) (27). Nelfinavir is water-soluble, and in rat studies, oral dosing was accomplished by daily gavage at 50 mg/kg in 5% dextrose or propylene glycol-water (27). These studies resulted in plasma $C_{max}$ values ranging from 1.34 to 1.65 μg/ml (2.33 to 2.87 μM). Because of slow absorption of nelfinavir, plasma levels were maintained for up to 7 hours after dosing.

Based upon equivalent surface area dosing in various animal models and humans, which originated from early quantitative comparisons of chemotherapeutic toxicity (28), an extrapolated equivalent dosing in mice (20 g) is 100 mg/kg ($C_{max}$ values≈2.5 μM in 150 g rats) to 500 mg/kg ($C_{max}$ values 7 μM in 60 kg humans). Consequently, oral dosing with daily gavage at 100 mg/kg in 5-7 mice is initiated at this initial dose level. Toxicities are noted in each mouse. Dosing escalates to 500 mg/kg as tolerated in the mice to establish the MTD. In selected mice at each dose level, pharmacokinetic studies are performed to determine the true $C_{max}$ values. Blood samples are obtained by cardiac puncture after appropriate sedation. Approximately 1 ml of blood is generally obtainable. Plasma (≈0.63 ml) is separated immediately after sampling by centrifugation and stored at −20° C. until analyzed. The plasma is processed by the Analytical Pharmacology Core Facility at City of Hope (Duarte, Calif.) on a Shimazdu LC-10A HPLC using a previously reported HPLC assay (27). The data is analyzed using the Shimazdu EZChrom software.

8. Evaluation of Nelfinavir-Mediated Inhibition of Liposarcoma Growth in SW872 Cells and Primary Human Liposarcoma Tumors In Vivo in the SCID-hu Murine Model.

CB-17 scid/scid (SCID) mice are used, with MTD for nelfinavir established in these mice as described above. The mice are used to establish xenografts with the human SW872 liposarcoma cell line and primary human liposarcomas. The establishment of primary human liposarcoma tumors in the SCID-hu murine mouse model is used to evaluate the value of nelfinavir in inhibiting primary human liposarcoma growth in vivo. The mice are anesthetized with a mixture of ketamine 50 mg/kg and xylazine HCl (2 to 5 mg/kg) administered intraperitoneally before any invasive procedure. A xenograft is considered established when more than three passages are obtained and regrowth is successful from tumor tissue frozen in liquid nitrogen. Upon establishment of the xenograft tumors, the mice are treated with nelfinavir to determine its in vivo efficacy.

$1\text{-}2\times10^6$ logarithmically-growing SW872 cells are implanted subcutaneously into both flanks of 8-10 week-old SCID-hu mice. Upon establishment of a 100 mm³ palpable tumor, oral dosing with daily gavage at the MTD-1 is initiated. 5-7 mice are treated at MTD-1. The increase in tumor volume from the start of treatment ($V_0$) until the value at any given time ($V_t$) is calculated and expressed as the relative tumor volume ($V_t/V_0$) on the day of measurement. The mean of these values are used to calculate the efficacy as a ratio between treated (T) and control (C) tumors (T/C×100%). Growth inhibition is expressed as 100%−(T/C×100%). The highest percentage reached on a particular day within 5 weeks after initiation of nelfinavir is considered the optimal growth inhibition. Dosing escalates to the MTD to determine whether dose-dependent inhibition is present in vivo. Mice are euthanized with $CO_2$ when the tumors become burdensome.

REFERENCES

Cited References

1. Jemal A, Murray T, Samuels A, Ghafoor A, Ward E, and Thun M J. Cancer statistics, 2003. CA Cancer J Clin 53: 5-26, 2003.
2. Coindre J-M, Terrier P, Guillou L, Le Doussal V, Collin F, Ranchère D, Sastre X, Vilain M-O, Bonichon F, and N'Guyen Bui B. Predictive value of grade for metastasis development in the main histologic types of adult soft tissue sarcomas: a study of 1240 patients from the French Federation of Cancer Centers Sarcoma Group. Cancer 91: 1914-1926, 2001.
3. Brennan M F, Casper E S, and Harrison L B. Soft tissue sarcoma. In: DeVita V T Jr., Hellman S, Rosenberg S A, eds. Cancer: Principles & Practice of Oncology. 6$^{th}$ ed. Philadelphia, Pa.: Lippincott-Raven Publishers: 1738-1887, 2001.
4. Sreekantaiah C, Ladanyi M, Rodriguez E, and Chaganti R S. Chromosomal aberrations in soft tissue tumors. Relevance to diagnosis, classification, and molecular mechanisms. Am J Pathol 144: 1121-1134, 1994.
5. Patel S R, Burgess M A, Plager C, Papadopoulos N E, Linke K A, and Benjamin R S. Myxoid liposarcoma: experience with chemotherapy. Cancer 74: 1265-1269, 1994.
6. Warrell R P, Frankel S R, Miller W H, Scheinberg D A, Itri L M, Hittelman W N, Vyas R, Andreeff M, Tafuri A, Jakubowski A, Gabrilove J, Gordon M S, and Dmitrovsky E. Differentiation therapy of acute promyelocytic leukemia with tretinoin (all-trans-retinoic acid). N Engl J Med 324: 1385-1398, 1992.
7. Tallman M S, Anderson J W, Schiffer C A, Appelbaum F R, Feusner J H, Ogden A, Shepherd L, Willman C, Bloomfield C D, Rowe J M, and Wiernik P H. All-trans-retinoic acid in acute promyelocytic leukemia. N Engl J Med 337: 1021-1028, 1997.
8. Tontonoz P, Singer S, Forman B M, Sarraf P, Fletcher J A, Fletcher C D M, Brun R P, Mueller E, Altiok S, Oppenheim H, Evans R M, and Spiegelman B M. Terminal differentiation of human liposarcoma cells induced by ligands for peroxisome proliferator-activated receptor γ and the retinoid X receptor. Proc Natl Acad Sci USA 94: 237-241, 1997.
9. Demetri G D, Fletcher C D M, Mueller E, Sarraf P, Naujoks R, Campbell N, Spiegelman B M, and Singer S. Induction of solid tumor differentiation by the peroxisome proliferator-activated receptor-γ ligand troglitazone in patients with liposarcoma. Proc Natl Acad Sci USA 96: 3951-8956, 1999.
10. Palella F J, Delaney K M, Moorman A C, Loveless M O, Fuhrer J, Satten G A, Aschman D J, Holmberg S D, and the HIV Outpatient Study Investigators. Declining morbidity and mortality among patients with advanced human immunodeficiency virus infection. N Engl J Med 338: 853-860, 1998.
11. Flexner C. HIV-protease inhibitors. N Engl J Med 338: 1281-1292, 1998.
12. Le Grice S F J, Mills J, and Mous J. Active site mutagenesis of the AIDS virus protease and its alleviation by trans complementation. EMBO J 7: 2547-2553, 1988.
13. Carr A, Samaras K, Burton S, Law M, Freund J, Chisholm D, and Cooper D A. A syndrome of peripheral lipodystrophy, hyperlipidaemia and insulin resistance in patients receiving HIV protease inhibitors. AIDS 12: F51-F58, 1998.
14. Carr A, Samaras K, Thorisdottir A, Kaufmann G R, Chisholm D J, and Cooper D A. Diagnosis, prediction, and natural course of HIV-1 protease-inhibitor-associated lipodystrophy, hyperlipidemia, and diabetes mellitus. Lancet 353: 2093-2099, 1999.
15. Carr A, Samaras K, Chisholm D J, and Cooper D A. Pathogenesis of HIV-1-protease inhibitor-associated peripheral lipodystrophy, hyperlipidaemia, and insulin resistance. Lancet 351: 1881-1883, 1998.
16. Zhang B, Macnaul K, Szalkowski D, Li Z, Berger J, and Moller D E. Inhibition of adipocyte differentiation by HIV protease inhibitors. J Clin Endocr Metab 84: 4274, 1999.
17. Riddle T M, Kuhel D G, Woollett L A, Fichtenbaum C J, and Hui D Y. HIV protease inhibitor induces fatty acid and sterol biosynthesis in liver and adipose tissues due to accumulation of activated sterol regulatory element-biding proteins in the nucleus. J Biol Chem 276: 37514-37519, 2001.
18. Caron M, Auclair M, Vigouroux C, Glorian M, Forest C, and Capeau J. The HIV protease inhibitor indinavir impairs sterol regulatory element-biding protein-1 intranuclear localization, inhibits preadipocyte differentiation, and induces insulin resistance. Diabetes 50: 1378, 2001.
19. Kim J B, and Spiegelman B M. ADD1/SREBP1 promotes adipocyte differentiation and gene expression linked to fatty acid metabolism. Genes Dev 10: 1096-1107, 1996.
20. Kim J B, Wright H M, Wright M, and Spiegelman B M. ADD1/SREBP1 activates PPARγ through the production of endogenous ligand. Proc Natl Acad Sci U.S.A. 95: 4333-4337, 1998.
21. Dowell P, Flexner C, Kwiterovich P O, and Lane M D. Suppression of preadipocyte differentiation and promotion of adipocyte death by HIV protease inhibitors. J Biol Chem 52: 41325-41332, 2000.
22. Figgitt D P, and Plosker G L. Saquinavir soft-gel capsule: an updated review of its use in the management of HIV infection. Drugs 60: 481-516, 2000.
23. Shih, C-C, Hu J, Arber D, LeBon T, and Forman S J. Transplantation and growth characteristics of human fetal lymph node in immunodeficient mice. Exp Hematol 28: 1046-1053, 2000.
24. McCune J M, Namikawa R, Kaneshima H, Shultz L D, Lieberman M, and Weissman I L. The SCID-hu mouse: murine model for the analysis of human hematolymphoid differentiation and function. Science 241: 1632-1639, 1988.
25. Tontonoz P, Hu, E, and Spiegelman B M. Stimulation of adipogenesis in fibroblasts by PPARγ2, a lipid-activated transcription factor. Cell 79: 1147-1156, 1994.
26. Gossen M, and Bujard H. Tight control of gene expression in mammalian cells by tetracycline-responsive promoters. Proc Natl Acad Sci U.S.A. 89: 5547-5551, 1992.
27. Shetty B V, Kosa M B, Khalil D A, and Webber S. Preclinical pharmacokinetics and distribution to tissue of AG1343, an inhibitor of human immunodeficiency virus type I protease. Antimicrob Agents Chemo 40: 110-114, 1996.
28. Freireich E J, Gehan E A, Rall D P, Schmidt L H, and Skipper H E. Quantitative comparison of toxicity of anticancer agents in mouse, rat, hamster, dog, monkey, and man. Cancer Chemo Reports 50: 219-244, 1996.
29. Antman K, Crowley J, Balcerzak S P, Rivkin S E, Weiss G R, Elias A, Natale R B, Cooper R M, Barlogie B, Trump D L, Doroshow J H, Aisner J, Pugh R P, Weiss R B, Cooper B A, Clamond G H, and Baker L H. An Intergroup phase III randomized study of doxorubicin and dacarbazine with or without ifosfamide and mesna in advanced soft tissue and bone sarcomas. J Clin Oncol 11: 1276-1285, 1993.
30. Atherton, D. J.; Pitcher, D. W.; Wells, R. S.; MacDonald, D. M.: A syndrome of various cutaneous pigmented lesions, myxoid neurofibromata and atrial myxoma: the NAME syndrome. *Brit. J. Derm.* 103: 421-429, 1980.
31. *Mendelian Inheritance in Man* (OMIN), http://www.ncbi.nlm.nih.gov/, OMIN reference numbers 160980 and 151900.

Other References

Borden E C, Baker L H, Bell R S, Bramwell V, Demetri G D, Eisenberg B L, Fletcher C D M, Fletcher J A, Ladanyi M, Meltzer P, O'Sullivan B, Parkinson D R, Pisters P W T, Saxman S, Singer S, Sundaram M, van Oosterom A T, Verweij J, Waalen J, Weiss S W, and Brennan M F. Soft tissue sarcomas of adults: state of the translational science. Clin Cancer Res 9: 1941-1956, 2003.

Bernstein E, Caudy A A, Hammond S M, and Hannon G J. Role for a bidentate ribonuclease in the initiation step of RNA interference. Nature 409: 363-366, 2001.

Chow W A, and Doroshow J H. The Ewing's family of tumors (EFT) express the KIT and PDGFR-$\alpha$ tyrosine kinase receptors. Proc Amer Assoc Cancer Res 43: 336a, 2002.

Chow W A, Wilczynski S P, and Doroshow J H. Receptor tyrosine kinase inhibition in Ewing's family of tumors. Proc Amer Assoc Cancer Res. 44: 4700a, 2003.

Flexner C. HIV-protease inhibitors. N Engl J Med 338: 1281-1292, 1998.

Koeffler H P. Peroxisome proliferator-activated receptor $\gamma$ and cancers. Clin Cancer Res 9: 1-9, 2003.

Shih, C C, Hu M C T, Hu J, Medeiros J, and Forman S J. Long-term Ex vivo maintenance and expansion of transplantable human hematopoietic stem cells. Blood 94: 1623-1636, 1999.

Shih, C C, Weng Y, Mamelak A, LeBon T, Hu M C T, and Forman S J. Identification of a candidate human neurohematopoietic stem-cell population. Blood 98: 2412-2422, 2001.

We claim:

1. A method of inhibiting growth of a liposarcoma in a subject comprising administering a therapeutically effective amount of a composition comprising HIV protease inhibitor to the subject, wherein the HIV protease inhibitor is indinavir, nelfinavir, or ritonavir.

2. The method of claim 1, wherein the composition comprises two or more of the HIV protease inhibitors selected from the group of indinavir, nelfinavir, and ritonavir.

3. The method of claim 1, wherein the HIV protease inhibitor is nelfinavir.

4. The method of claim 1, wherein the composition comprising HIV protease inhibitor is administered in conjunction with chemotherapy.

5. The method of claim 1, wherein the composition comprising HIV protease inhibitor is administered in conjunction with radiotherapy.

6. The method of claim 1, wherein the composition comprising HIV protease inhibitor is administered in conjunction with both chemotherapy and radiotherapy.

7. The method of claim 1, wherein the composition comprising HIV protease inhibitor is administered after surgical removal of the liposarcoma.

8. The method of claim 1, wherein the composition comprising HIV protease inhibitor is administered before surgical removal of the liposarcoma.

9. The method of claim 1, wherein the composition comprising HIV protease inhibitor is administered in a pharmaceutically acceptable carrier.

10. A method of inhibiting growth of a liposarcoma in a patient comprising administering a therapeutically effective amount of a composition comprising nelfinavir in a pharmaceutically acceptable carrier to the patient.

11. The method of claim 10, wherein the nelfinavir is administered in conjunction with chemotherapy, radiotherapy, or a combination of both chemotherapy and radiotherapy.

12. The method of claim 10, wherein the nelfinavir is administered after surgical removal of the liposarcoma.

13. The method of claim 10, wherein the nelfinavir is administered before surgical removal of the liposarcoma.

* * * * *